United States Patent
Wakamori

(10) Patent No.: US 7,382,901 B2
(45) Date of Patent: Jun. 3, 2008

(54) EYE IMAGE IMAGING DEVICE

(75) Inventor: Masahiro Wakamori, Yokohama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 530 days.

(21) Appl. No.: 10/525,185

(22) PCT Filed: Sep. 28, 2004

(86) PCT No.: PCT/JP2004/014572

§ 371 (c)(1),
(2), (4) Date: Feb. 22, 2005

(87) PCT Pub. No.: WO2005/032371

PCT Pub. Date: Apr. 14, 2005

(65) Prior Publication Data

US 2005/0264758 A1  Dec. 1, 2005

(30) Foreign Application Priority Data

Oct. 1, 2003 (JP) .............................. 2003-343021

(51) Int. Cl.
*G06K 9/00* (2006.01)

(52) U.S. Cl. .................................................. 382/117
(58) Field of Classification Search ..................... None
See application file for complete search history.

(56) References Cited

U.S. PATENT DOCUMENTS

| | | | |
|---|---|---|---|
| 5,953,440 A | | 9/1999 | Zhang et al. |
| 5,978,494 A | * | 11/1999 | Zhang .......................... 382/117 |
| 6,095,989 A | * | 8/2000 | Hay et al. .................... 600/558 |
| 2002/0131622 A1 | * | 9/2002 | Lee et al. ..................... 382/106 |
| 2003/0012413 A1 | * | 1/2003 | Kusakari et al. ............. 382/117 |

FOREIGN PATENT DOCUMENTS

| | | |
|---|---|---|
| JP | 2000-131598 | 5/2000 |
| JP | 2002-085382 | 3/2002 |
| JP | 2002-094865 | 3/2002 |
| JP | 2002-334325 A | 11/2002 |
| JP | 2003-263629 * | 9/2003 |
| JP | 2003-263629 A | 9/2003 |
| JP | 2003-331265 A | 11/2003 |
| JP | 2004-220069 A | 8/2004 |

OTHER PUBLICATIONS

Japanese Search Report for PCT/JP2004/014572, dated Nov. 2, 2004.

* cited by examiner

*Primary Examiner*—Charles Kim
(74) *Attorney, Agent, or Firm*—RatnerPrestia

(57) ABSTRACT

An eye image taking device comprises: an imaging unit for taking an eye of a user as an eye image; a focusing degree calculating unit for calculating the magnitude of high-frequency components from the eye image; a threshold setting unit for setting a focusing threshold intrinsic to an authorized user; and a focus deciding unit for deciding a focus by comparing the magnitude of the high-frequency components and the focusing threshold, so that the optimum focusing threshold is set for the authorized user.

7 Claims, 7 Drawing Sheets

EYE IMAGE IMAGING DEVICE

This application is a U.S. National Phase Application of PCT International Application PCT/JP2004/014572.

TECHNICAL FIELD

The present invention relates to an eye image taking device and, more particularly, to an eye image taking device which can be installed in a mobile terminal device.

BACKGROUND ART

Generally, the iris authentication identifies a person by illuminating the eye of a user or its circumference with a near infrared ray or the like, by taking the eye image and the circumference image (as will be generally called the "eye image") with a camera, by extracting the iris information from the eye image obtained, and by comparing the iris information with the iris information which has already been registered in the iris information database. The eye image taking device to be used has to take the eye image highly precisely for extracting the iris information of the user precisely. Thus, there has been proposed an eye image taking device, which utilizes the automatic focusing technique to detect the eye position from the taken image of the entire face and to take the eye image of a desired size by zooming up that eye with a zoom lens.

In this automatic focusing technique, the control is made by making use of the fact that many high-frequency components are contained in image signals if an object is focused (as will be called the "focusing") so that the contour image is clearly taken, by integrating the high-frequency components in the image signals while varying the lens position, and by searching the lens position, at which the integrated value is the maximum. In order to search the lens position promptly, moreover, there is generally adopted (as referred to JP-A-2000-131598, for example) the so-called "hill-climbing method", in which the lens position is gradually varied in the direction for the high-frequency components to increase.

In recent years, on the other hand, as the accounts settling system or the like using a mobile terminal device such as a mobile telephone spreads, it has been tried to install the iris authenticating function of a high personal authentication reliability in the mobile terminal device. However, the eye image taking device needs a drive system for driving the lens and has a difficulty in reducing the size and weight of the optical system. It has, therefore, been extremely difficult to install the eye image taking device having the automatic focusing mechanism in the mobile terminal device such as the mobile telephone. For these reasons, a practical eye image taking device for the mobile terminal device can be proposed by installing a small, light and inexpensive camera using a fixed focus lens, by deciding the focusing degree with the magnitude of the high-frequency components contained in the image signals, and by guiding the imaging distance so that the magnitude of the high-frequency components may be larger than a predetermined threshold value.

However, personal differences are large not only in the pattern of an iris and the shapes of the individual portions such as eyelashes or eyelids but also in the magnitude of the high-frequency components contained in the eye image signals. Therefore, the method for guiding the imaging distance so that the magnitude of the high-frequency components may become larger than the predetermined threshold value has a problem that the stable focus decision cannot be attained depending upon the shapes of the individual portions of the eye of the user. This problem is exemplified such that some user may fetch the eye image out of focus or can neither attain the focus decision nor fetch the eye image.

The present invention contemplates to solve the problems thus far described and has an object to provide an eye image taking device, which can make a stable focus decision irrespective of the shapes of the individual portions of the eye of a user by using the small, light and inexpensive fixed focus lens and which can be installed in a mobile terminal device.

DISCLOSURE OF THE INVENTION

According to the invention, there is provided an eye image taking device comprising: an imaging unit for taking an eye image of a user; a focusing degree calculating unit for calculating a focusing degree from the eye image taken at the imaging unit; a threshold setting unit for setting a focusing threshold intrinsic to an authorized user; and a focus deciding unit for deciding a focus by comparing the focusing degree and the focusing threshold, wherein the threshold setting unit sets the focusing threshold on the basis of the eye image of the authorized user.

DETAILED DESCRIPTION OF PREFERRED EMBODIMENTS

Eye image taking devices according to embodiments of the invention will be described with reference to the accompanying drawings.

Embodiment 1

Figure 1:
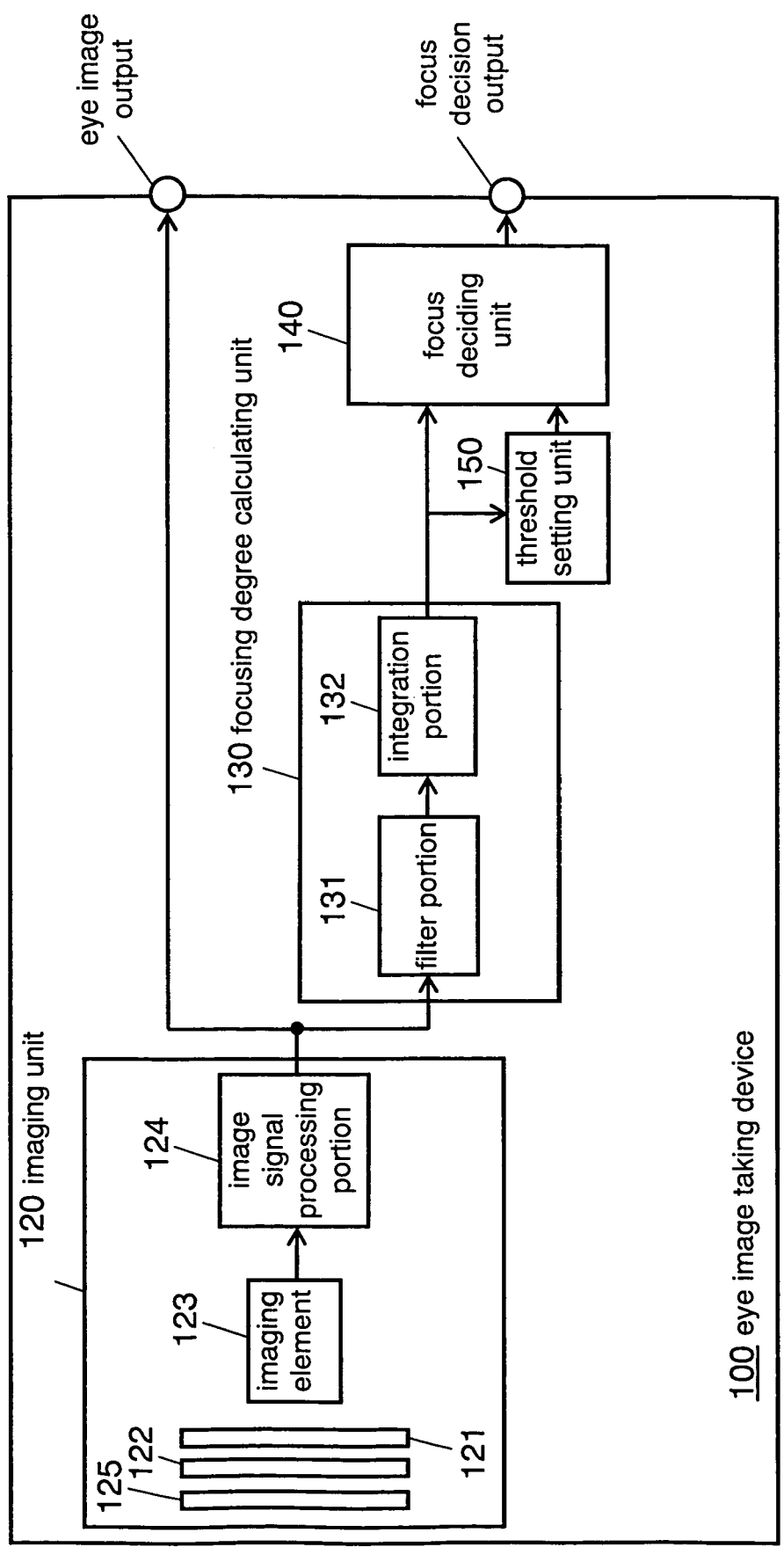
FIG. 1 is a block diagram showing a configuration of an eye image taking device according to Embodiment 1 of the invention.

FIG. 1 is a block diagram showing a configuration of an eye image taking device according to Embodiment 1 of the invention. Eye image taking device 100 in Embodiment 1 is provided with: imaging unit 120 for taking an eye image of the user; focusing degree calculating unit 130 for calculating the magnitude of a high-frequency component contained in the eye image, as a focusing degree; threshold setting unit 150 for setting a focusing threshold intrinsic to an authorized user; focus deciding unit 140 for deciding the focus by comparing the focusing degree and the focusing threshold; and an illumination unit (although not shown) for illuminating the eye of the user and its circumference by irradiating a near infrared ray in a quantity suited for the eye image acquisition.

Imaging unit 120 includes lens 121, visible light cut filter 122, imaging element 123, image signal processing portion 124 and guide mirror 125. In Embodiment 1, a fixed focus lens is used as lens 121 to reduce the size, weight and cost of the optical system. Guide mirror 125 guides the eye of the user to a correct imaging position when the user reflects his or her eye on guide mirror 125. The eye of the user is taken on imaging element 123 through lens 121 and visible light cut filter 122. Image signal processing portion 124 extracts image signal components from the output signals of imaging element 123 and subjects the image signal components as the image signals for gain adjustments to a necessary processing. Image signal processing portion 124 outputs the processed image signals as the eye image signals of the user.

Focusing degree calculating unit 130 includes filter portion 131 and integration portion 132. Filter portion 131 extracts signals of high-frequency components having a predetermined frequency band suited for the focusing decision, from the image signals outputted by image signal processing portion 124, and outputs the extracted high-frequency component signals to integration portion 132. Integration portion 132 integrates the square value or absolute value of the high-frequency components obtained through filter portion 131, within the area of one screen (or one frame), and outputs the integrated value as the magnitude of the high-frequency components contained in the eye image. The magnitude of the high-frequency components outputted from integration portion 132 and contained in the eye image will be called "focusing degree F".

Focus deciding unit 140 performs the decision of focus by comparing focusing degree F with predetermined focusing threshold Fth by a method, as will be described hereinafter. Thus, the focus deciding output obtained as the output of focus deciding unit 140 and the eye image output or the output of image signal processing portion 124 are inputted to the iris authenticating device (although not shown) so that the iris authentication is made by using the eye image signals which have been decided as the focus.

Threshold setting unit 150 sets focusing threshold Fth in the following manner for the authorized user of a mobile terminal device having eye image taking device 100 of Embodiment 1 of the invention installed therein, such as the terminal use contractor or the terminal owner. When the authorized user registers the iris information, eye images are taken at first at varied distances between eye image taking device 100 and the eye thereby to obtain a plurality of eye images corresponding to different imaging distances X, and focusing degrees F are determined for the individual eye images. Threshold setting unit 150 determines maximum Fmax from plural focusing degrees F thus obtained, and determines focusing threshold Fth by multiplying maximum Fmax by a predetermined coefficient, as will be described hereinafter. In case the authorized user changes with transfers or the like, focusing threshold Fth has to be reset when the new authorized user makes a registration of the iris information again in the iris authenticating device.

Figure 2:
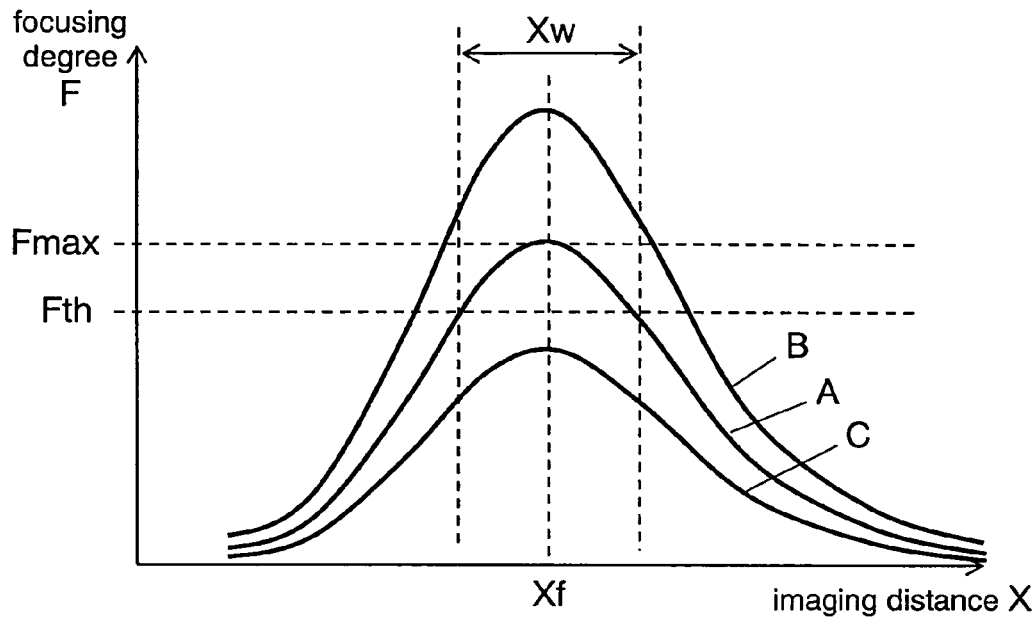
FIG. 2 is a diagram schematically showing relations between a focusing degree and an imaging distance for different users.

Here will be described the reason why focusing threshold Fth is set for the authorized user. FIG. 2 is a diagram schematically showing relations between imaging distance X for different users and focusing degree F. Letters A, B and C designate the relations among three different users. In Embodiment 1, the fixed focus lens is used as lens 121. Therefore, imaging distance Xf, at which focusing degree F takes the maximum, is determined by the focal distance (i.e., the distance of just focus) of the fixed focus lens and is common among the users. However, the relations between focusing degree F and imaging distance X are different among individuals, as shown in FIG. 2. This is partly because the iris patterns are different among individuals so that the high-frequency components contained in the eye images are different among individuals and partly because the high-frequency components are influenced by portions other than the iris, such as eyelashes or eyelids.

In order to acquire the eye image, which is focused for each authorized user of each eye image taking device, therefore, maximum Fmax of the focusing degree intrinsic to each user has to be determined to take the image at distance Xf, at which focusing degree F is Fmax. In the practical use, however, it is hard to take the eye image at that distance Xf for maximum focusing degree F. It is, therefore, practical to authenticate the eye image, which has been focused for a practically trouble-free iris authentication although focusing degree F has failed to take the maximum, by assuming that the eye image is focused.

FIG. 2 shows this range of imaging distance X as focal range Xw. If the focusing threshold is set at the value indicated by Fth in FIG. 2, it is proper as the focusing threshold for user A to authenticate the eye image, for which focusing degree F exceeds focusing threshold Fth, i.e., the eye image which is within focal range Xw. For user B, on the contrary, an eye image, as cannot be authenticated, may be taken as the eye image which can be authenticated. For user C, on the other hand, the focus decision cannot be obtained. This makes it necessary to set intrinsic focusing threshold Fth optimum for the authorized user. By thus determining focusing threshold Fth, it is possible to attain an effect to lower the authentication factor (or another accepting factor) of the unauthorized user (i.e., users B and C shown in FIG. 2).

Even if the users are different, as shown in FIG. 2, the relations between focusing degree F and imaging distance X present generally similar shapes. So far as focusing degree F is within the range from maximum Fmax of the focusing degree to a value smaller at a predetermined ratio, imaging distance X may be within focal range Xw. Therefore, focusing threshold Fth can be determined by multiplying maximum Fmax by a predetermined coefficient. In this embodiment, it is assumed that the coefficient is set at 0.8, namely, that the eye image falls within the focal range if focusing degree F is 80% or more of Fmax. If the coefficient to multiply maximum Fmax becomes larger, a more focused satisfactory eye image can be obtained, but the focusing range is narrowed to make it hard to obtain the focus deciding result. Thus, the value of the coefficient is desired to be suitably set according to the optical characteristics of imaging unit 120 or the characteristics of the iris authenticating device to be connected, and the using purpose of the iris authenticating device.

Figure 3:
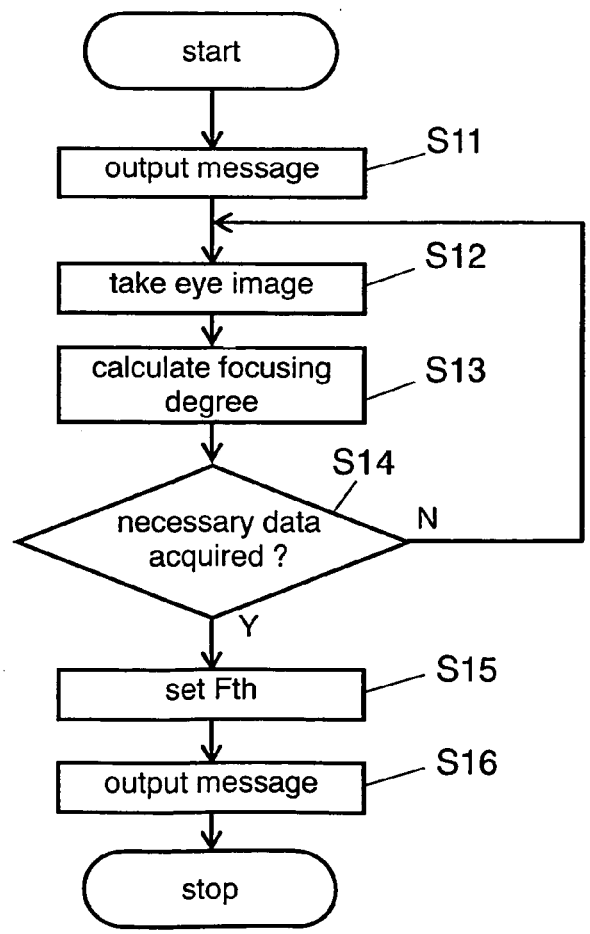
FIG. 3 is a flow chart showing an operating procedure at a focusing threshold setting time in Embodiment 1 of the invention.

Here will be described a procedure for determining focusing threshold Fth. FIG. 3 is a flow chart showing an operating procedure at a focusing threshold setting time in Embodiment 1 of the invention.

First of all, a message to start the focusing threshold setting is outputted (at S11). At this focusing threshold setting time, plural eye images of different imaging distances are needed. The message to be outputted is "Bring Camera Slowly toward Eye from Arm-Extended Position." This message may be either displayed by using a display unit such as a liquid crystal display panel attached to the mobile terminal device or outputted as a speech through an accessory speaker.

Next, the eye image of the user is taken (at S12), and the integrated value, i.e., focusing degree F of the high-frequency components contained in the acquired eye image is determined (at S13). It is the decided (at S14) whether or not the data necessary for setting the focusing threshold have been acquired. The series operations from Step S12 to Step S14 are repeated till the data necessary for setting the focusing threshold are acquired. The data necessary for setting the focusing threshold at this time are focusing degree F of the plural eye images, which have been taken within the range of the imaging distance containing focal range Xw and longer than focal range Xw. The description is made on the case, in which the images are consecutively taken by bringing the camera gradually closer from the distant position. The image taking operations are started from that of an eye image having low focusing degree F. The data are on focusing degrees F of the plural eye images, in which focusing degree F becomes gradually larger and becomes again smaller after it exhibited maximum Fmax.

Maximum Fmax is determined from the data of plural focusing degrees F, and focusing threshold Fth is set (at S15) by multiplying maximum Fmax by the predetermined coefficient (i.e., 0.8 in this embodiment). At last, a message indicating the end of the threshold setting is outputted by an image or speech (at S16). Thus, focusing threshold Fth intrinsic to the authorized user can be set for the authorized user.

By thus setting focusing threshold Fth at the optimum value intrinsic to the authorized user, the focused eye image can be reliably acquired even with the small, light and inexpensive fixed focus lens.

In another method for setting focusing threshold Fth, a scale cut to the length of the focal distance can be used at the focusing threshold setting time. Then, the focusing threshold can be more simply set in case the eye image can be taken with the imaging distance being fixed at focal distance Xf for the just focus. The high-frequency components contained in the eye image at this time exhibit maximum Fmax. Therefore, focusing threshold Fth may be set by multiplying maximum Fmax by the coefficient (0.8).

Of eye image taking device 100 in Embodiment 1, the operations of the focusing decision at the iris authenticating time will be briefly described in the following. It is assumed that focusing threshold Fth has already been set.

At first, the eye image is taken to determine the high-frequency components contained, i.e., focusing degree F. If this value is at focusing threshold Fth or higher, it is decided that a focused eye image has been obtained, and the eye image output is outputted together with the focus deciding output to the iris authenticating device. In case focusing degree F is lower than focusing threshold Fth, the eye image is taken again. At this time, a message to change imaging distance X may be outputted to the user.

Embodiment 2

Figure 4:
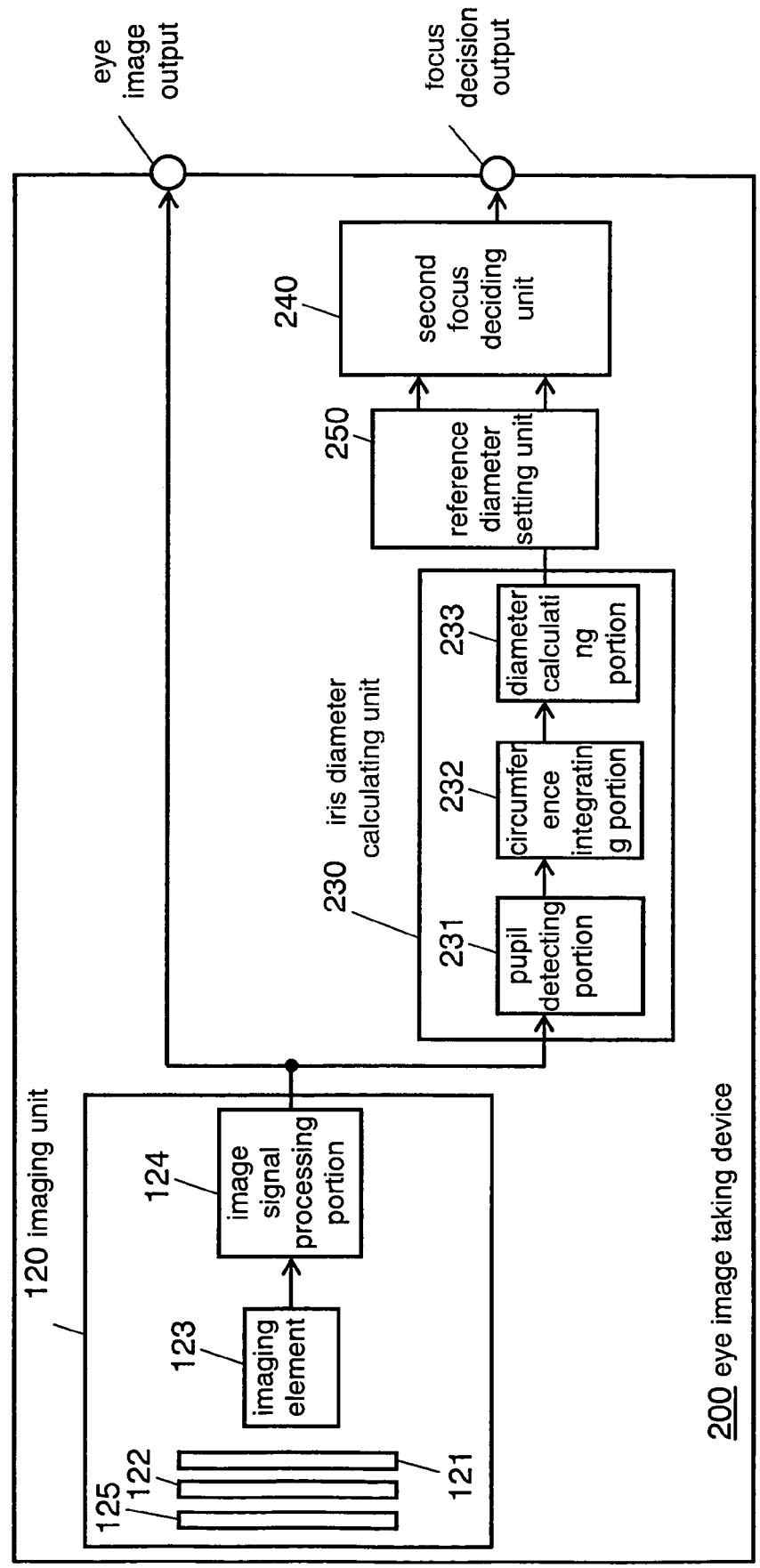
FIG. 4 is a block diagram showing a configuration of an eye image taking device according to Embodiment 2 of the invention.

FIG. 4 is a block diagram showing a configuration of an eye image taking device according to Embodiment 2 of the invention. Blocks identical to those of Embodiment 1 are designated by the common reference numerals. The eye image taking device of Embodiment 2 is largely different from the eye image taking device of Embodiment 1 in that the focus decision is made on the basis of not focusing degree F of the eye image but iris diameter R of the eye image. Eye image taking device 200 in Embodiment 2 is provided with: imaging unit 120; iris diameter calculating unit 230 for calculating the iris diameter of each eye image; reference diameter setting unit 250 for setting the reference iris diameter intrinsic to the authorized user; and focus deciding unit 240 (as will be called the "second focus deciding unit" so that it may be discriminated from the focus deciding unit in Embodiment 1) for deciding the focus by comparing the iris diameter and the reference iris diameter.

Iris diameter calculating unit 230 includes pupil detecting portion 231, circumference integrating portion 232 and diameter calculating portion 233. Iris detecting portion 231 binarizes the acquired eye image to extract a low luminance area, decides the pupil from the shape and size of the area, and determines the central coordinates of the area to set the coordinates as the pupil center. Circumference integrating portion 232 integrates the eye image circumferentially around the iris center, and diameter calculating portion 233 finds the boundary point between the iris and the white portion from the circumferentially integrated values and outputs the boundary point as iris diameter R.

Second focus deciding unit 240 decides the focus by comparing iris diameter R calculated from the eye image, with reference iris diameter Rf, which has been determined in advance by a method, as will be described hereinafter. In case the eye image to be used for the authentication is not obtained, it is decided according to the magnitude relation between iris diameter R and reference iris diameter Rf whether the imaging distance is to be increased or decreased so as to acquire an eye image of a high focusing degree.

Reference diameter setting unit 250 sets reference iris diameter Rf in the following manner for the authorized user of the mobile terminal device, in which eye image taking device 200 in Embodiment 2 of the invention is installed. At first, a measure having the focusing distance drawn therein is used to fix the distance between the eye image taking device and the eye at focal distance Xf or the just focus. Then, the eye image is taken by imaging unit 120, and iris diameter R is calculated by iris diameter calculating unit 230. Reference diameter setting unit 250 sets this iris diameter R as reference iris diameter Rf.

Figure 5:
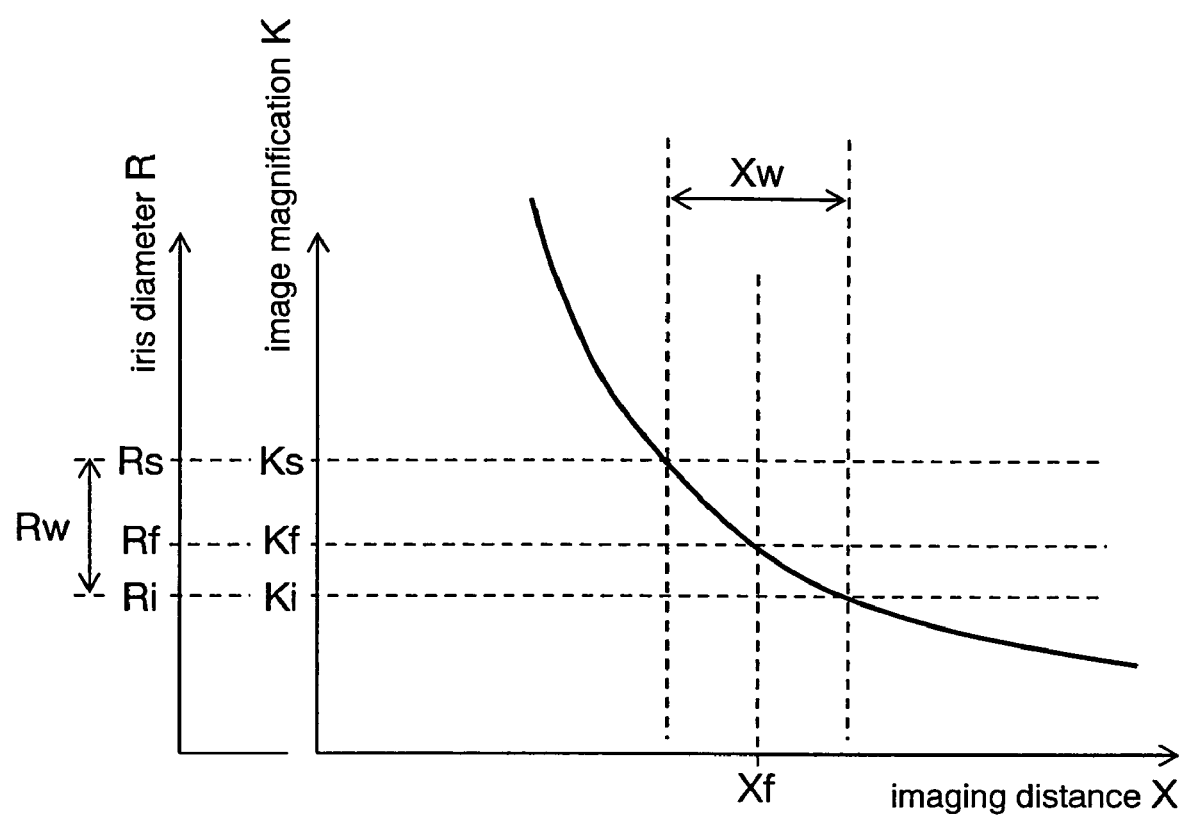
FIG. 5 is a diagram showing relations of the magnification of an image to be taken and an iris.diameter to an imaging distance.

FIG. 5 is a diagram showing relations of imaging distance X, and magnification K of an image to be taken and iris diameter R. Here: letters Kf designate the magnification of an image at imaging distance Xf; letters Ks and Ki designate the upper limit and the lower limit of the magnification of the image within focal range Xw; letters Rf designate the iris diameter at imaging distance Xf; and letters Rs and Ri designate an upper limit and a lower limit of the iris diameter in focal range Xw. Generally in the imaging unit using the fixed focus lens, magnification K is small in case imaging distance X is large, but is large in case imaging distance X is small. These relations are predetermined by the optical system used in the imaging unit. On the other hand, iris diameter R and magnification K are proportional to each other, and iris diameter R is not varied by the change or the like in the environment so that the focus decision using iris diameter R can be made by knowing iris diameter Rf in focal distance Xf.

In Embodiment 2 like Embodiment 1, it is difficult in the practical use to take the image at that distance Xf, in which the imaging distance is the just focus. It is, therefore, practical to perform the authentication while assuming that the eye image is focused, if the focus is got within the iris authentication without any practical trouble. FIG. 5 designates such an allowable range of the iris diameter by Rw as corresponds to focal range Xw of that imaging distance.

If allowable range Rw is excessively widened, the authentication is difficult in this case, too, because an eye image out of focus is taken. If narrowed, on the contrary, a better focused satisfactory eye image is obtained, but the focal range becomes narrower so that the focus decision becomes harder. Thus, allowable range Rw of the iris diameter is desired to be suitably set according to the optical characteristics of imaging unit 120, the characteristics of the iris authenticating device to be connected, and the using purpose of the iris authenticating device.

In eye image taking device 200 in Embodiment 2, the iris diameter is calculated from the eye image so that the number of calculations becomes larger than that of the calculation of the focusing degree. In case the acquired eye image does not fall in the focusing range, on the contrary, it is advantageous to know whether the iris diameter is too larger or smaller. In this case, therefore, it is known whether or not the camera should be brought closer or farther, so that the message to guide to a proper imaging distance can be given to the user.

As shown in FIG. 5, imaging distance X and magnification K of the image to be taken are made to correspond one-to-one in the relation, which is determined by the optical system used in the imaging unit, and iris diameter R and magnification K correspond one-to-one if limited to the authorized user. By knowing the iris diameter in the known imaging distance such as iris diameter Rf in focal distance Xf, therefore, imaging distance X can be calculated back from the value of iris diameter R.

Embodiment 3

Figure 6:
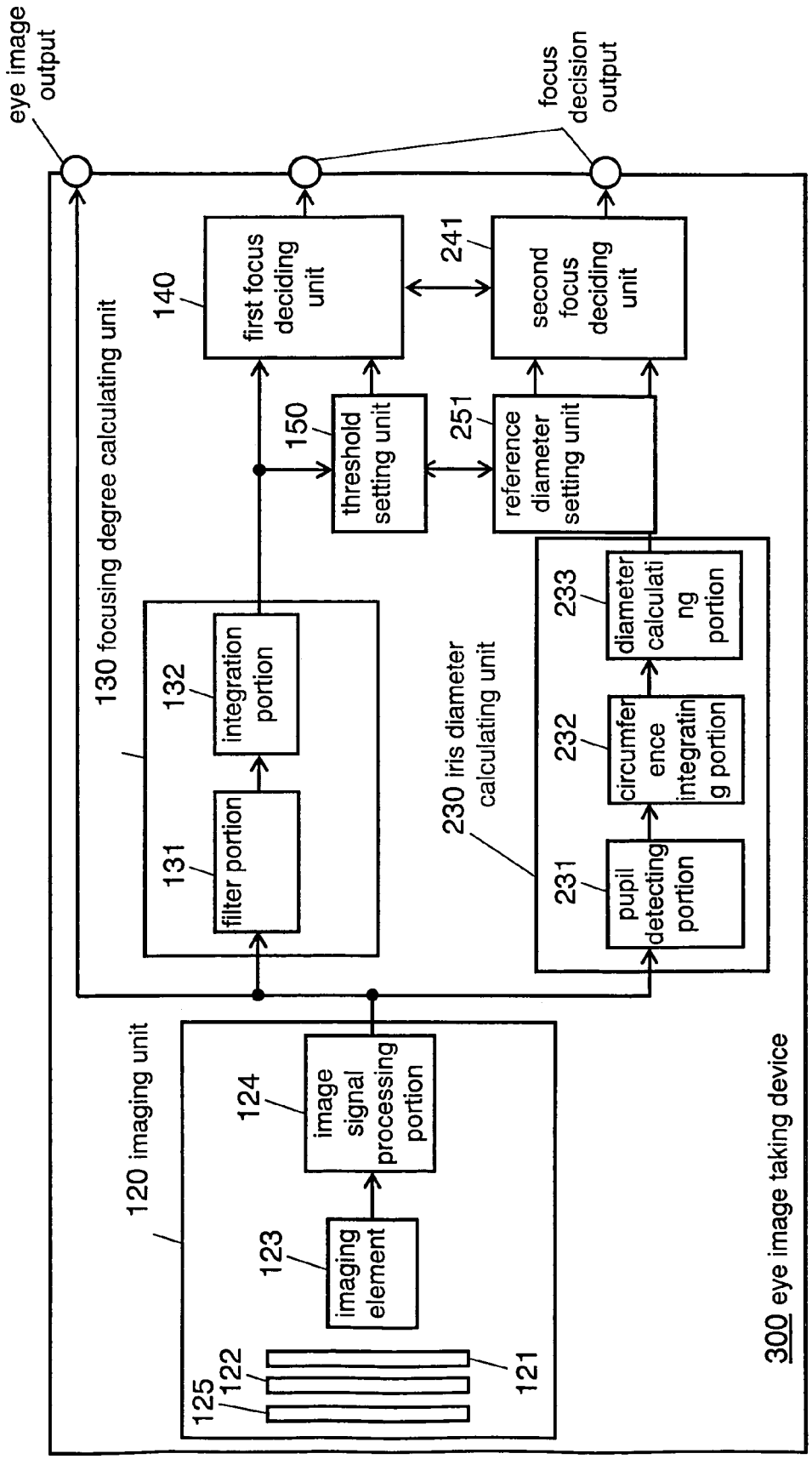
FIG. 6 is a block diagram showing a configuration of an eye image taking device according to Embodiment 3 of the invention.

FIG. 6 is a block diagram showing a configuration of an eye image taking device according to Embodiment 3 of the invention. The same blocks as those of Embodiment 1 and Embodiment 2 are designated by the common reference numerals.

Eye image taking device 300 in Embodiment 3 is provided with: imaging unit 120; focusing degree calculating unit 130; threshold setting unit 150; focus deciding unit 140 (as will be called the "first focus deciding unit") 140; iris diameter calculating unit 230; second focus deciding unit 241; and reference diameter setting unit 251. Thus, the circuit blocks of eye image taking device 300 in Embodiment 3 are provided with the circuit blocks of the eye image taking device of Embodiment 1 and the circuit blocks of the eye image taking device of Embodiment 2.

Reference diameter setting unit 251 sets reference iris diameter Rf in the following manners for the authorized user of the mobile terminal device, which has eye image taking device 300 of Embodiment 3 of the invention installed therein. At first, eye images are taken at different imaging distances X to obtain plural eye images corresponding to different imaging distances X, and focusing degrees F are determined for the individual eye images. From the plural eye images, the eye image having maximum focusing degree F is determined, and its iris diameter R is calculated so that its value is used as reference iris diameter Rf.

The reasons for thus setting the reference iris diameter Rf are that the imaging distance, at which focusing degree F takes maximum Fth, is focal distance Xf, as has been described in Embodiment 1, and that iris diameter R of the eye image taken at focal distance Xf can be set as reference iris diameter Rf, as has been described in Embodiment 2.

Figure 7:
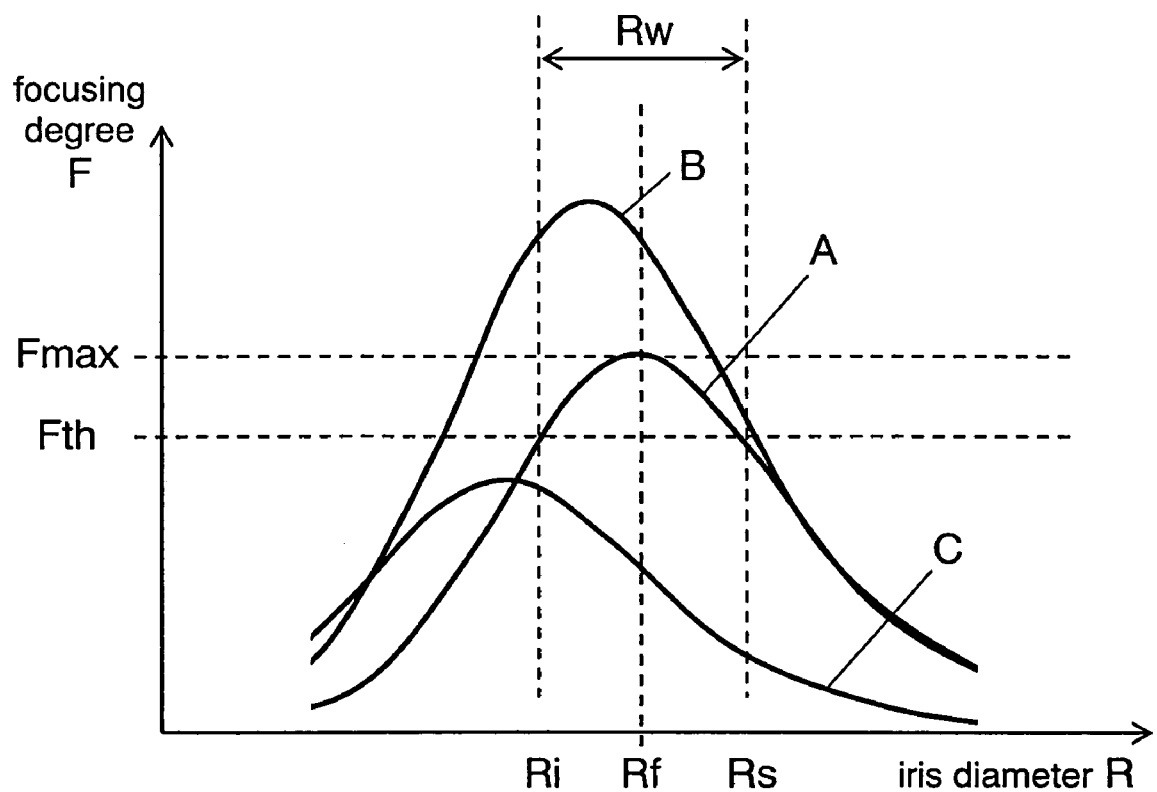
FIG. 7 is a diagram schematically showing relations between an iris diameter and a focusing degree for different users.

FIG. 7 is a diagram schematically showing relations between iris diameter R and focusing degree F for different users, and letters A, B and C designate the three users shown in FIG. 2. FIG. 7 is different from FIG. 2 in that the abscissa indicates not imaging distance X but iris diameter R. The reason why iris diameters Rf at the time when focusing degree F indicates maximum Fmax are different for the individual users is that the iris sizes are different for the individual users. In this example, it is indicated that user A has the largest iris and that user C has the smallest iris. FIG. 7 plots reference iris diameter Rf, allowable range Rw (having upper limit Rs and lower limit Ri) of the iris diameter, and focusing threshold Fth for user A or the authorized user.

In this case, too, an effect to lower the authentication factor for the non-authorized users (i.e., users B and C of FIG. 7) can be obtained, as has been described in connection with Embodiment 1, by optimizing allowable range Rw of the iris diameter and focusing threshold Fth for authorized user A.

Figure 8:
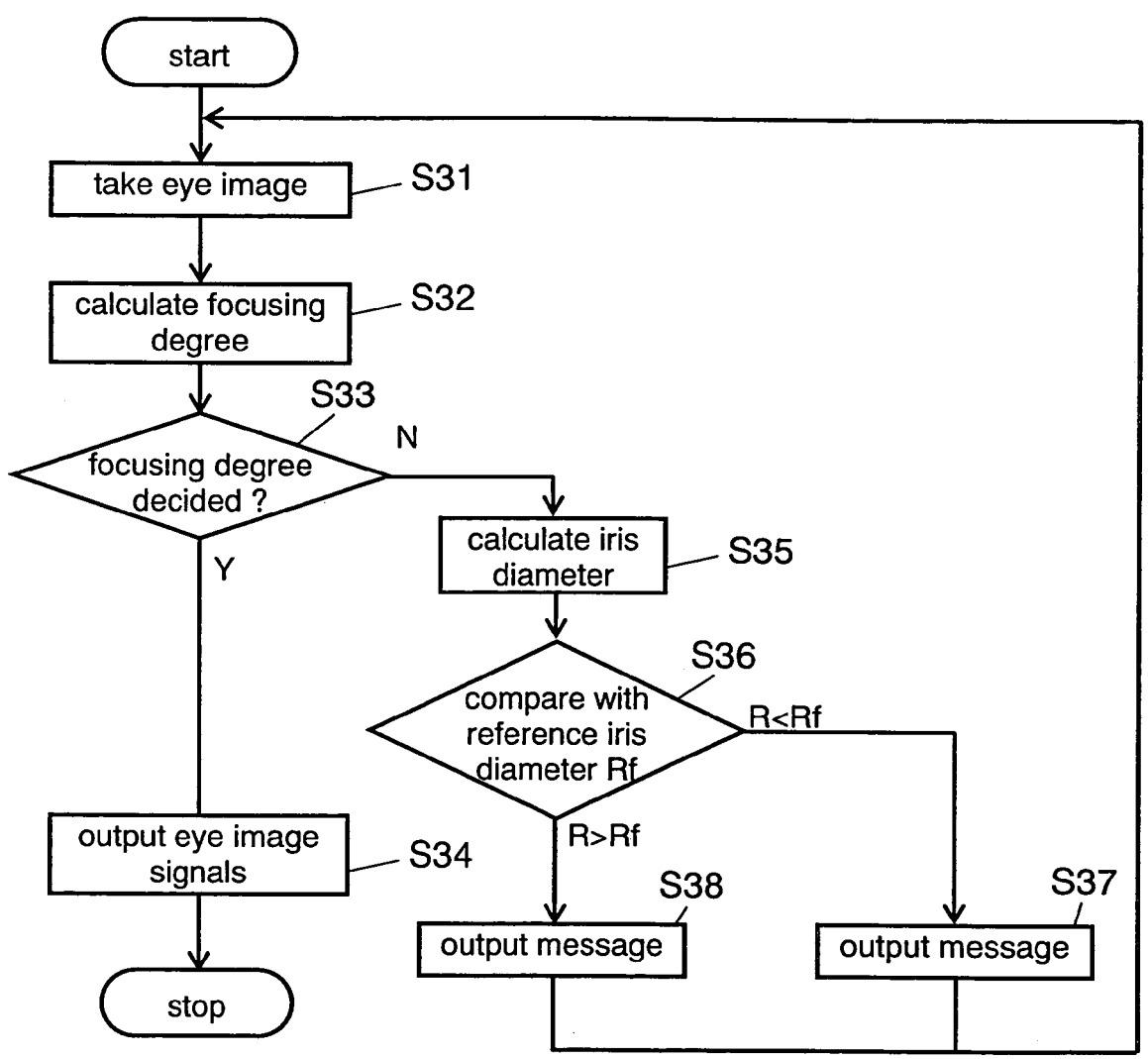
FIG. 8 is a flow chart showing an iris image taking procedure at an iris authenticating time in Embodiment 3 of the invention.

Here will be described the operations of eye image taking device 300 of Embodiment 3 for the focus decisions at the iris authenticating time. It is assumed that focusing threshold Fth and reference iris diameter Rf have already been set. FIG. 8 is a flow chart showing an eye image taking procedure of the eye image taking device in Embodiment 3 of the invention at the iris authenticating time.

First of all, the eye image of the user is taken (at S31) to determine focusing degree F of the acquired eye image (at S32). This focusing degree F is compared with focusing threshold Fth to decide (at S33) whether or not the acquired eye image is such an focused image as can be authenticated on the iris. In case focusing degree F is focusing threshold Fth or higher, an authenticatable eye image can be acquired. Therefore, the eye image signals are outputted together with the focus decision result to the iris authenticating device (at S34). In case focusing degree F is lower than focusing threshold Fth, iris diameter R of the acquired eye image is determined (at S35) and is compared with reference iris diameter Rf (at S36). In case iris diameter R is smaller than reference iris diameter Rf, a message to bring the camera closer to the eye is outputted (at S37), and the procedure returns to Step S31. In case iris diameter R is larger than reference iris diameter Rf, on the other hand, a message to bring the camera apart from the eye is outputted (at S38), and the procedure returns to Step S31.

By thus using the small, light and inexpensive fixed focus lens, it is possible to take the eye image, which makes the iris authentication possible.

In the flow chart shown in FIG. 8, the procedure always advances to Step S35, in case focusing degree F does not satisfy focusing threshold Fth at Step S33. However, the procedure to advance from Step S33 to Step S35 may be only once for several times and may otherwise advance from Step S33 to Step S31.

The following advantages are attained from eye image taking device 300 of Embodiment 3, which is provided with the two decision units of first focus deciding unit 140 and second focus deciding unit 241. The calculations of focusing degree F necessary for deciding first focus deciding unit 140 can be executed by the relatively simple ones to extract and integrate the high-frequency components. Therefore, the time period for the calculations can be shortened so that the calculations on the image signals inputted can be performed in real time. In case, however, the imaging distance of the eye image fails to fall within the focused range, whether or not the camera is brought closer cannot be known from the value of focusing degree F. On the other hand, the calculations of iris diameter R necessary for the decision of second focus deciding unit 241 are made at first by determining the iris center from the eye images and then by performing the circumferential integration thereby to identify the iris diameter. Thus, the time period for the calculations is elongated. On the contrary, the imaging distance can be estimated to inform which way the camera is to be moved in order to obtain the focused eye image. Therefore, the focus decision is made by first focus deciding unit 140 of the shorter calculation time. In case the focus decision cannot be obtained, the decision of second focus deciding unit 241 is made to inform the user in which way the camera is to be moved. It is possible to attain the eye image, which is focused for a short time.

In the description thus far made, the eye image for highest focusing degree F is derived from the plural eye images of different imaging distances, and its iris diameter R is used as reference iris diameter Rf. However, focusing threshold Fth, and upper limit Rs and lower limit Ri of the allowable range of the iris diameter may be determined in the following manners.

When the authorized user registers the iris information, the eye image is taken at first by varying the distance of the eye image taking device from the eye, to calculate focusing degrees F and iris diameters R, which are contained in the individual eye images. Next, an approximate function F=F(R) indicating the relation between focusing degrees F and iris diameters R, which are determined from the plural eye images. From sets of two iris diameters R1 and R2 of equal focusing degrees i.e. F(R1)=F(R2), moreover, there is selected the set, in which the ratio of R2/R1 of the iris diameters is equal to the ratio of Ki/Ks of the image magnifications. Values R1 and R2 of the iris diameters are set to upper limit Rs and lower limit Ri of the allowable range of the iris diameters, and focusing degree F at this time is set to focusing threshold Fth.

Here, the relation between focusing degree F and iris diameter R need not to be functionally approximated. However, the data of focusing degrees F and iris diameters R, which are obtained from the plural eye images, are discrete. If that relation is approximated by the continuous function, therefore, the calculations can be made easy, and the data can be interpolated. Thus, the advantage obtained is that focusing threshold Fth, and allowable range Rs and Ri of the iris diameter can be more precisely set.

If the allowable range of the iris diameter and focusing threshold Fth thus set are used, an advantage is that the decision results of the first focus deciding unit and the second focus deciding unit are substantially identical.

According to the invention, it is possible to provide the eye image taking device, which can make a stable focus decision irrespective of the shape of the eye of the user by using the small, light and inexpensive fixed focus lens and which can be installed in the mobile terminal device.

INDUSTRIAL APPLICABILITY

The eye image taking device of the invention can make a stable focus decision irrespective of the shape of the eye of the user by using the small, light and inexpensive fixed focus lens and can be installed in the mobile terminal device. Thus, the invention is useful in an eye image taking device, especially in the eye image taking device which can be installed in the mobile terminal device.

The invention claimed is:

1. An eye image taking device comprising:
   an imaging unit for taking an eye image of a user;
   a focusing degree calculating unit for calculating a focusing degree from the eye image taken at the imaging unit;
   a threshold setting unit for determining a focus range including a lower limit of an optimum focusing threshold intrinsic to an authorized user and that excludes other users; and
   a focus deciding unit for deciding a focus by comparing the focusing degree and the focus range,
   wherein the threshold setting unit sets the focusing threshold on the basis of the eye image of the authorized user;
   wherein the focusing degree calculating unit calculates the magnitude of the high-frequency components contained in the eye image taken by the imaging unit, as the focusing degree, and wherein the threshold setting unit selects the maximum from a plurality of focusing degrees, which are calculated individually from the plural eye images of different imaging distances for the authorized user, thereby to set the focusing threshold on the basis of the maximum.

2. An eye image taking device according to claim 1,
   wherein the threshold setting unit sets the focusing threshold on the basis of the focusing degree which is calculated from the eye images taken at the focal distance for the authorized user.

3. An eye image taking device comprising:
   an imaging unit for taking an eye image of a user;
   an iris diameter calculating unit for calculating an iris diameter in the eye image;
   a reference diameter setting unit for setting a reference iris diameter; and
   a focus deciding unit for deciding a focus by using the iris diameter and the reference iris diameter,
   wherein the reference diameter setting unit sets the reference iris diameter intrinsic to an authorized user and that excludes other users on the basis of the eye image of the authorized user, and
   wherein the focus deciding unit decides the focus by comparing the iris diameter and an iris diameter range including an upper limit and a lower limit of an optimum iris diameter, and corresponding to a focal range of an imaging distance at which the eye is imaged.

4. An eye image taking device according to claim 3,
   wherein the reference diameter setting unit sets the value of the iris diameter, which is calculated from the eye images taken at the focal distance for the authorized user, as the reference iris diameter.

5. An eye image taking device comprising:
   an imaging unit for taking an eye image of a user;
   a focusing degree calculating unit for calculating a focusing degree from the eye image taken at the imaging unit;
   a threshold setting unit for determining a focus range including a lower limit of an optimum focusing threshold intrinsic to an authorized user and that excludes other users;
   a first focus deciding unit for deciding a focus by comparing the focusing degree and the focus range;
   an iris diameter calculating unit for calculating an iris diameter in the eye image;
   a reference diameter setting unit for setting a reference iris diameter; and a second focus deciding unit for deciding the focus by using the iris diameter and the reference iris diameter, wherein the reference diameter unit sets the reference iris diameter intrinsic to the authorized user and that excludes other users on the basis of the eye image of the authorized user, wherein the second focus deciding unit decides the focus by comparing the iris diameter and an iris diameter range including an upper limit and a lower limit of an optimum iris diameter, and wherein the focus decision is made at the second focus deciding unit in case the decision of the focus cannot be obtained at the first focus deciding unit; wherein the focusing degree calculating unit calculates the magnitude of the high-frequency components contained in the eye image taken by the imaging unit, as the focusing degree, and wherein the threshold setting unit selects the maximum from a plurality of focusing degrees, which are calculated individually from the plural eye images of different imaging distances for the authorized user, thereby to set the focusing threshold on the basis of the maximum.

6. An eye image taking device according to claim 5, wherein the reference diameter setting unit sets the iris diameter in the eye image of the maximum focusing degree of the plural eye images of different imaging distances, as the reference iris diameter for the authorized user.

7. An eye image taking device according to claim 5, wherein the reference diameter setting unit sets the values of such two of the plural iris diameters calculated individually from the plural eye images of different imaging distances as have an equal focusing degree and an iris diameter ratio equal to a predetermined value, as two reference iris diameters for the authorized user, and wherein the threshold setting unit sets the focusing degree as the focusing threshold.

\* \* \* \* \*